United States Patent [19]
Fetter

[11] Patent Number: 5,735,691
[45] Date of Patent: Apr. 7, 1998

[54] DEVICES FOR PERSONAL HYGIENE AND PROFESSIONAL ORAL CARE

[76] Inventor: Carolyn M. Fetter, 15 Renee Ct., Edison, N.J. 08820

[21] Appl. No.: 634,827

[22] Filed: Apr. 19, 1996

[51] Int. Cl.⁶ .................... A61C 5/14; A61B 1/24
[52] U.S. Cl. .................. 433/140; 600/238; 15/145
[58] Field of Search .............. 433/93, 140; 15/167.1, 15/167.2, 143.1, 145; 600/237–239, 242, 243; D4/104, 129; D7/648

[56] References Cited

U.S. PATENT DOCUMENTS

| | | | |
|---|---|---|---|
| D. 299,386 | 1/1989 | Jacobs | D4/129 |
| 527,235 | 10/1894 | Carpi | 600/238 |
| 2,220,674 | 11/1940 | Bloomheart | 600/238 |
| 2,595,462 | 5/1952 | Johnson | 24/116 A |
| 3,483,619 | 12/1969 | Smith | 600/238 |
| 3,722,101 | 3/1973 | Via, Jr. | 600/238 |
| 3,971,370 | 7/1976 | Halford et al. | 600/237 |
| 4,041,937 | 8/1977 | Diaz . | |
| 4,219,331 | 8/1980 | Getz | 433/140 |
| 4,283,808 | 8/1981 | Beebe | 15/145 |
| 4,523,781 | 6/1985 | Brody | 294/1.1 |
| 4,802,851 | 2/1989 | Rhoades . | |
| 4,975,057 | 12/1990 | Dyfvermark . | |
| 4,992,046 | 2/1991 | Sharp . | |
| 5,094,616 | 3/1992 | Levenson . | |
| 5,152,686 | 10/1992 | Dugan et al. . | |
| 5,205,733 | 4/1993 | Scheels | 433/140 |
| 5,466,153 | 11/1995 | Poindexter | 433/140 |

FOREIGN PATENT DOCUMENTS

| | | | |
|---|---|---|---|
| 2840429 | 3/1980 | Germany | 15/145 |
| 94018902 | 9/1994 | WIPO | 433/140 |

OTHER PUBLICATIONS

"Complete Ableware Catalog" by Maddak, Inc. Cat. #1294 pp. 33, P18,53.

*Primary Examiner*—Ralph Lewis
*Attorney, Agent, or Firm*—Mathews, Collins Shepherd & Gould

[57] ABSTRACT

A hygiene implement handle formed of a compressible material includes an aperture for receiving a hygiene implement. Alternatively, a mouth prop handle apparatus has a handle and mouth prop formed integrally to one another of a compressible material. A rigid core is positioned within the compressible material. A mouth prop having a wedge shape can also be formed of the compressible material. The compressible material can be a foam material. The mouth prop handle and hygiene implement handle are disposable and can be advantageously used for special needs patients.

7 Claims, 10 Drawing Sheets

DEVICES FOR PERSONAL HYGIENE AND PROFESSIONAL ORAL CARE

BACKGROUND OF THE INVENTION

1. Field of the Invention

This invention relates to devices for personal hygiene, professional health care and activities of daily living, such as toothbrushes, razors, mouth props, dental mirrors, and cleansing devices.

2. Discussion of the Prior Art

Conventional manual hygiene articles, such as razors and toothbrushes, have been manufactured with the "normal" person without disabilities in mind. The handle of these articles is typically formed of a hard plastic resin and is formed into a slim shape which is suitable for a person with no dexterity problems. In high volume, the use of these materials is very cost-effective. However, the manufacture of a specialized item, such an a enlarged handle on a toothbrush for use by a person with a disability, such as arthritis or cerebral palsy, is impractical due to the high up-front cost for manufacturing. In the case of conventional mainstream items, the cost of this up-front capital can be amortized across millions of items. In the case of specialized items, however, a large up-front expenditure is not warranted because anticipated volumes are much lower and cannot support the investment.

In addition, specialized hygiene articles often require more material to produce the devices than material needed for conventional articles. For example, an enlarged toothbrush or razor handle which is suitable for a person with arthritis will be formed of a greater amount of material than for a similar item of conventional size. The amount of material required to build-up a device can make it heavy, which is disadvantageous for use by persons with dexterity problems.

One solution to the manufacturing problem of speciality devices has been for therapists or care givers for people with dexterity problems to use "normal" implements such as toothbrushes and razors and "build up" the grip to provide for better control. An acrylic material has been used to permanently build up the handle. Rubber-like foam tubing manufactured by Maddak, Inc., Paquannock, N.J., such as which comes in a roll can be cut to size and applied to the handle. Alternatively, molded pre-fabricated receptacles with straps have also been used on speciality items. Also, a gripping tube manufactured by Maddak, Inc. is formed of a durable plastic tube. Implement handles fit into the plastic tube. The above-described approaches can be expensive, as well as adding to the weight of the item. Other conventional solutions have used tennis balls and soda cans cut with a hole into which personal care items can be placed such that the tennis ball or soda can enlarge the grip of the item.

In particular, dental professionals who treat young children or patients with physical and mental handicaps have a need for specialized items. For example, people with cognitive deficiencies, such as those with Mental Retardation or Alzheimer's disease are often not able to keep their mouths open during dental procedures, and will sometimes be very resistive to the efforts of dental professionals. Conventional mouth props manufactured by McKesson, MDT Biologic Co., Anaheim, Calif. which are currently on the market are small and have a wedge shape. The conventional mouth props are typically constructed of metal covered with rubber. This conventional mouth prop has the disadvantage that in order to use the mouth prop the professional must place his or her fingers in the patient's mouth, thereby placing their fingers at risk of being injured if the patient becomes resistive. The conventional mouth prop also has the disadvantage that a fearful patient who bears down very hard on the rubber can ruin the mouth prop. In addition, when the rubber of the mouth prop is autoclaved (heat-sterilized), it disintegrates rapidly, causing the mouth piece to be unusable since the metal is exposed to the user. Also, this conventional mouth prop is expensive to manufacture.

Dental professionals also use a ratchet type mouth prop which locks the mouth in an open position. One example of a ratchet type mouth prop is manufactured by Hu Freidy, Chicago, Ill., as the "Molt moth prop". The end of the ratchet which is placed on the teeth is covered with a rubber tubing which helps protect the mouth from the metal of the mouth prop. The rubber of this mouth prop is also subject to disintegration from either the beating down by the patient or the heat of the autoclave. When the rubber fittings wear out, the entire mouth prop is subject to disposal unless the dental professional can devise a method for coveting the ends with a different rubber fitting.

U.S. Pat. No. 4,975,057 ('057) describes a dental appliance in the form of a bite block. Integrally formed in the bite block is an aperture for receiving an aspiration device.

U.S. Pat. No. 4,992,046 ('046) relates to a dental mouth prop for maintaining the jaws of a dental patient open while working on a tooth. The prop is formed of a rigid, hard, non-porous plastic. The '057 and '046 patents have the shortcomings that if the props were used with special needs patients, it would be difficult for the care provider to hold the props in place.

Other dental professionals have solved the needs of their special patients by forming a prop through bundling up a number of tongue depressors with gauze and tape. This solution provides the means to keep the mouth open and also provides the user with a handle so that the fingers do not need to go into the mouth.

A jawlock product entitled Bite Block® manufactured by Sage Product, Inc., Crystal Lake, Ill. has been used to keep the tongue in place during patient seizures. The jawlock product has a die-cut foam head and a tongue depressor which is glued into the foam as a handle. The jawlock device has been used by dental professionals for propping the mouth. The jawlock device has the drawback that when glue is used to assemble the product, it is difficult, if not impossible, to avoid getting excess glue on the handle and sometimes on the head. This creates an unappealing appearance for a product. Both the taped together tongue depressors and the jawlock device have the disadvantage that the wood from the tongue depressor can splinter and cause potential problems for both the hand of the professional and the mouth and tongue of the patient.

Of general relevance are U.S. Pat. Nos. 4,949,457; 4,802,851 and 4,041,937.

It is desirable to provide an inexpensive apparatus having an appropriate shape and formed of a durable disposable material for the use by people with disabilities and their caregivers, as well as professionals who treat special needs patients.

SUMMARY OF THE INVENTION

Briefly described, the invention relates to a hygiene implement handle formed of a compressible material. An aperture is formed in the handle for receiving the hygiene implement. The implement can include a tooth brush, a razor or other small handled personal care devices.

Alternatively, the invention relates to a mouth prop formed of a compressible material. The mouth prop has a wedge shape for mirroring the shape of the jaw and the mouth. A rigid core is positioned within the material for providing stability of the mouth prop. A plurality of depressions are formed in the mouth prop for holding open the teeth or jaw.

In one embodiment, a handle is formed integrally with the mouth prop. The handle is also formed of the compressible material. Preferably, this embodiment is used with special care patients to enable the patient care provider to manually hold the prop inside the mouth. The hygiene implant handle and mouth prop are disposable.

The compressible material has a compression strength in the range of about 10 to about 100 pounds per square inch. Preferably, the material is foam material formed of polyethylene or polyolefin.

The invention will be more fully described by reference to the following drawings.

DETAILED DESCRIPTION OF THE INVENTION

During the course of this description like numbers will be used to identify like elements according to the different figures which illustrate the invention.

Figure 1A:
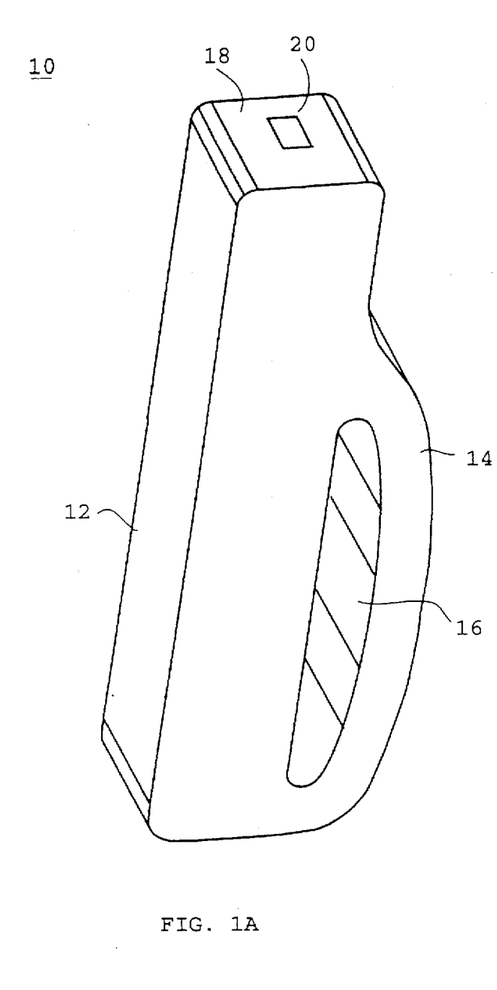
FIG. 1A is a front elevational view of a hygiene implement handle in accordance with the teachings of the present invention.
Figure 1B:
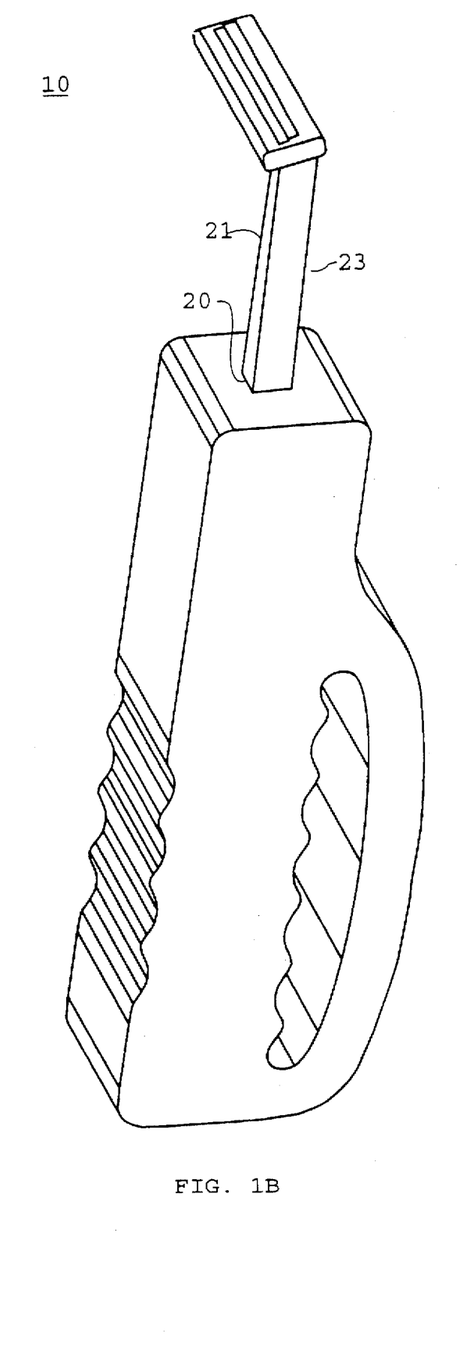
FIG. 1B is a from elevational view of a hygiene implement handle holding a razor.
Figure 1C:
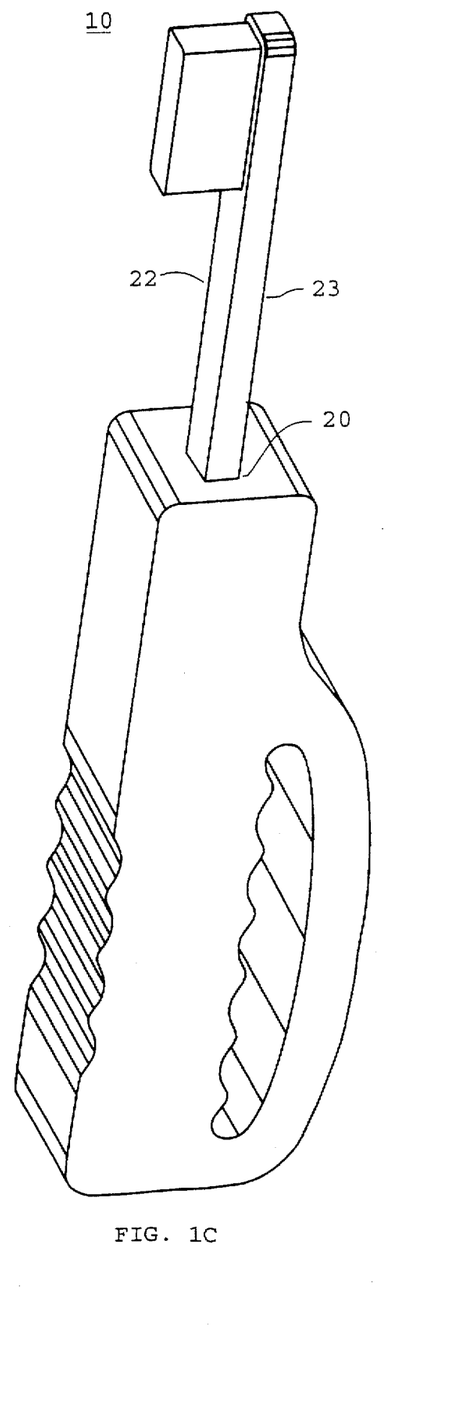
FIG. 1C is a front elevational view of a hygiene implement handle holding a toothbrush.
Figure 1D:
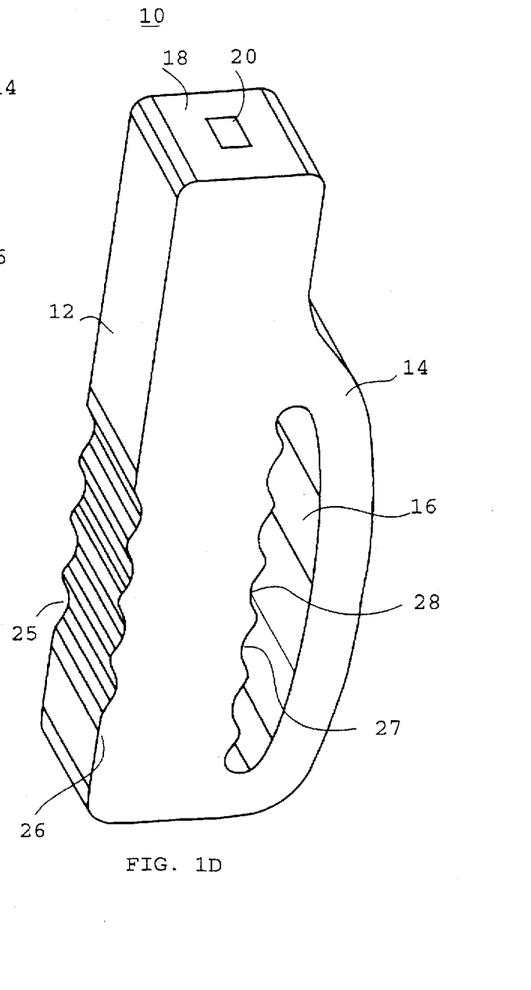
FIG. 1D is a front elevational view of a hygiene implement handle having depressions for gripping the handle.

FIGS. 1A–1D are elevational views of a hygiene implement handle 10. Body 12 includes handle 14 integral therewith. Aperture 20 in top surface 18 receives a hygiene implement. Aperture 20 surrounds body 23 of a hygiene implement, such as razor 21 or toothbrush 22, to hold the implement securely in hygiene implement handle 10. Preferably, as shown in FIG. 1D, a plurality of depressions 25 are formed on side surface 26 and a plurality of depressions 27 are formed on handle surface 28 for providing an improved grip. Opening 16 receives the fingers of a user of the hygiene implement handle 10 and the user's palm holds handle surface 28. Handle 14 fits around the knuckles of the user. Hygiene implement handle 10 can be used by special needs patients for making it easer to hold hygiene implements.

Figures 2A, 2B, 2C:
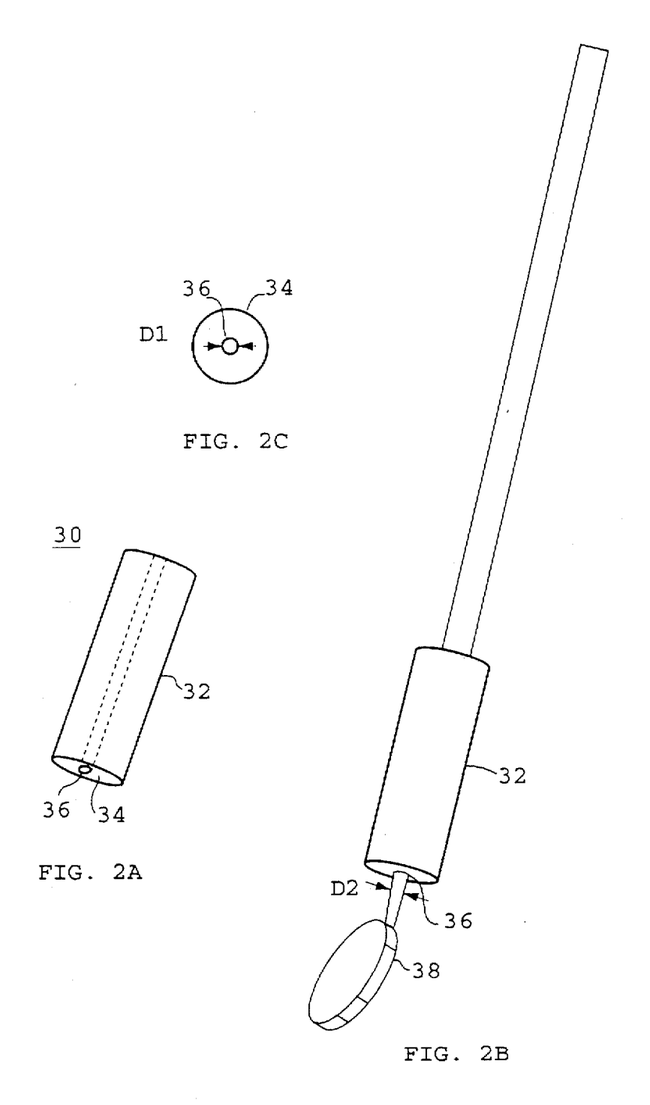
FIG. 2A is a front elevational view of an alternate embodiment for a hygiene implement handle holding a dental mirror.
FIG. 2B is a perspective view of the handle shown in FIG. 2A.
FIG. 2C is a top view of the handle shown in FIG. 2A.

FIGS. 2A–2C illustrate an alternate embodiment of a hygiene implement handle 30 which surrounds a hygiene implement. Cylinder 32 includes aperture 36 therethrough which receives the hygiene implement. Aperture 36 has a diameter $D_1$ which is comparable to diameter $D_2$ of the hygiene implant such as dental mirror 38 shown in FIG. 2C.

Figure 3A:
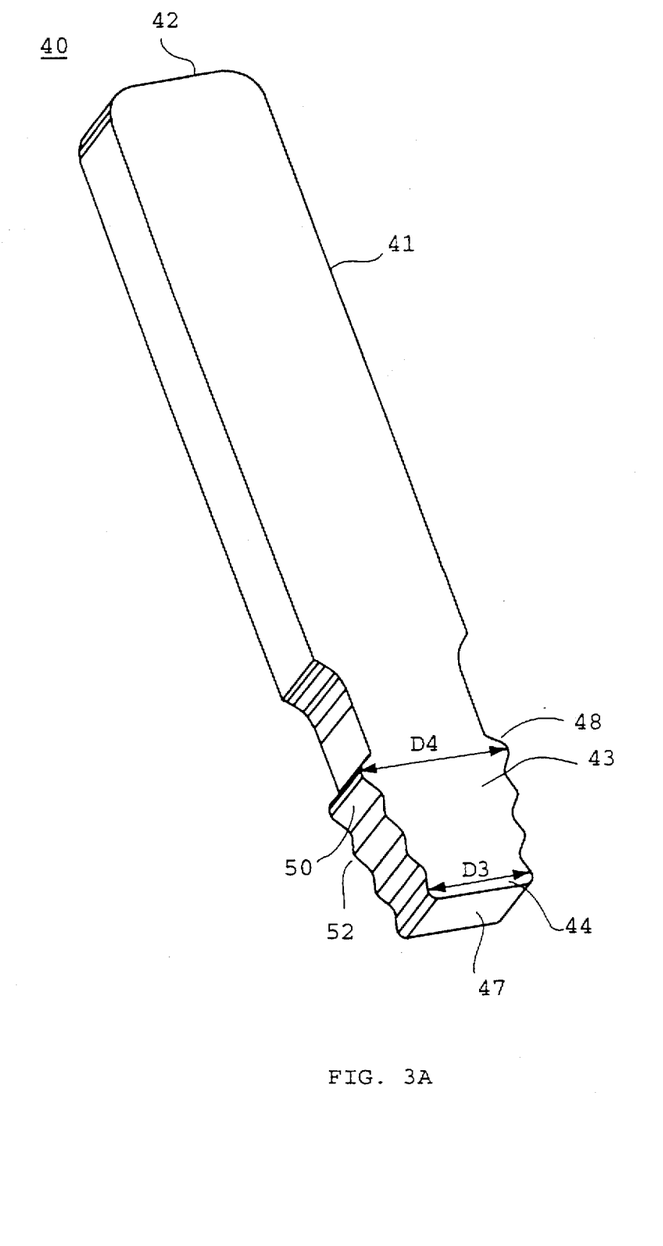
FIG. 3A is a front elevational view of a mouth prop handle apparatus in accordance with the present invention.

FIG. 3A is an elevational view of mouth prop handle apparatus 40 in accordance with the teachings of the present invention. In this embodiment, mouth prop handle apparatus 40 includes handle 41 at end 42 integrally formed with mouth prop 43 at end 44. A plurality of depressions 50 are formed on side 52 of mouth prop 43 for holding open the jaws of a patient and provide a comfortable yet secure surface upon which to rest the teeth. Preferably, mouth prop 43 has a wedge shape with bottom end 47 having a width $D_3$ which is smaller than width $D_4$ at portion 48 of mouth prop 43 for mirroring the shape of the mouth and jaw, thereby allowing the user to maintain oral access.

Figure 3B:
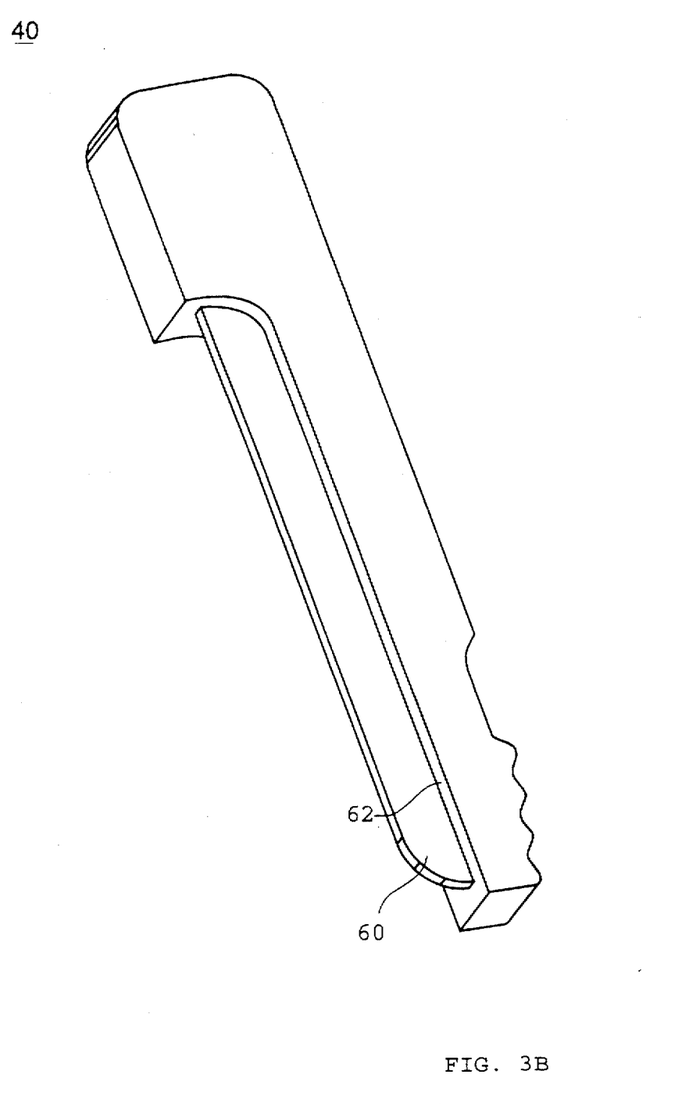
FIG. 3B is a cut away view of a mouth prop handle apparatus shown in FIG. 3A.

FIG. 3B illustrates a cut away view of mouth prop handle apparatus 40. Core 60 is disposed within mouth prop handle apparatus 40. Core 60 is surrounded by compressible material 62 for forming mouth prop handle apparatus 40. Core 60 is formed of a rigid material. Preferably, core 60 is formed of wood or hard plastic for providing stability and strength. Compressible material 62 can be formed of a moderately compressible material. Preferably, compressible material 62 is a foam material such as polyolefin and polyethylene. Most preferably, material 62 is inexpensive to manufacture and is disposable. Preferably, the compressible material has a compression strength between about 10 and about 100 psi. Material 62 is lightweight and provides comfort to the user while providing control of the handle.

Figure 3C:
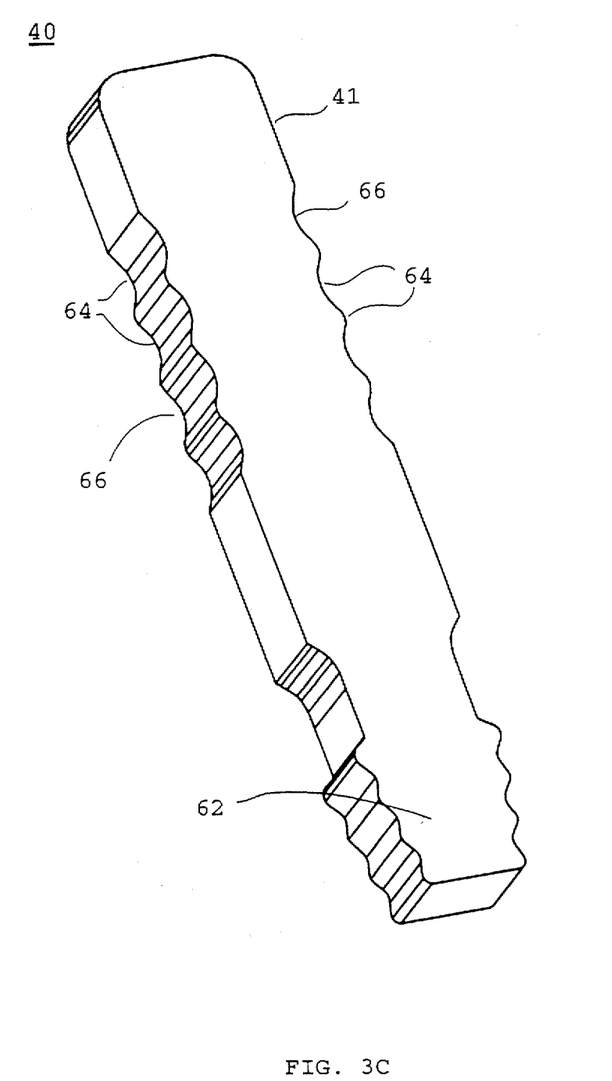
FIG. 3C is a from elevational view of a mouth prop handle apparatus having depressions in the handle.

Preferably, as shown in FIG. 3C, handle 41 has a plurality of depressions 64 formed in side surfaces 66 for receiving the fingers of the care person using the mouth prop handle apparatus 40.

In a preferred embodiment, material 62 can be die-cut to form mouth prop handle apparatus 40. Alternatively, material 62 can be molded to form mouth prop handle apparatus 40. A flavorant, such as mint, root beer or grape, can be added to material 62 during the manufacturing process. Preferably, mouth prop handle apparatus 40 is used with patients having difficulty keeping their mouths open to enable the patient care provider to manually hold the prop in place inside the jaws of the patient.

Figures 4A, 4B:
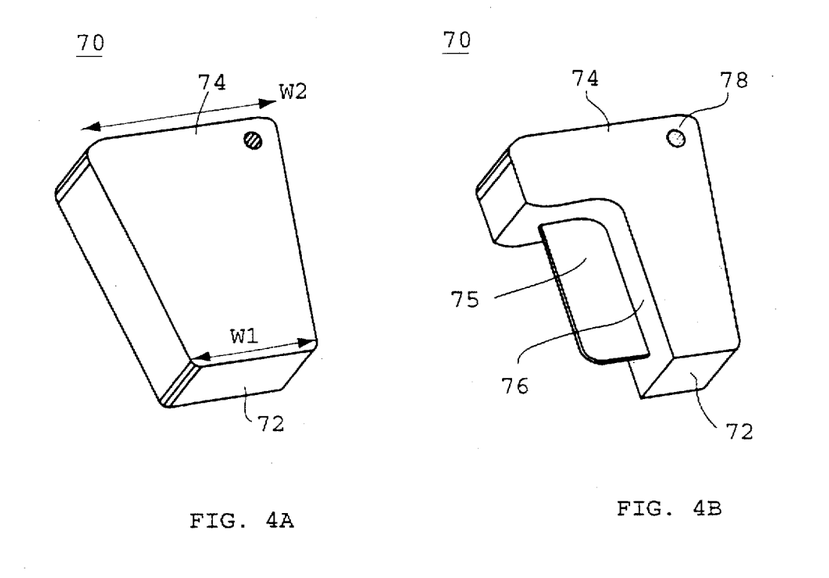
FIG. 4A is a front elevational view of a mouth prop.
FIG. 4B is a cut away view of the mouth prop shown in FIG. 4A.
Figure 4C:
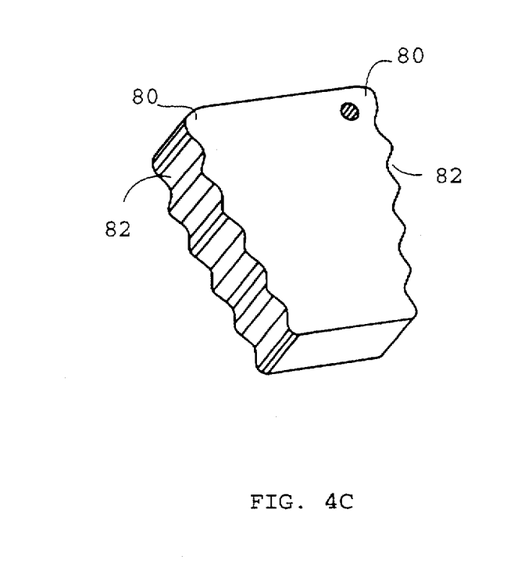
FIG. 4C is a front elevational view of a mouth prop having depressions in the side surfaces thereof.

FIGS. 4A through 4C illustrate mouth prop 70. Core 75 is disposed within material 76. Preferably, core 75 and material 76 are formed of similar materials to core 60 and material 62 described above. Mouth prop 70 has a wedge shape with end 72 having a smaller width $W_1$ than width $W_2$ of end 74. Aperture 78 can receive a string such as dental floss to prevent mouth prop 70 from falling into the airway during a dental procedure. Mouth prop 70 can be preferably used when a handle is not required to hold the mouth prop inside the jaws of the patient. Sides 80 can have a plurality of depressions 82 for holding open the jaws of the patient and to provide a comfortable yet secure surface, as shown in FIG. 4C.

Figure 5A:
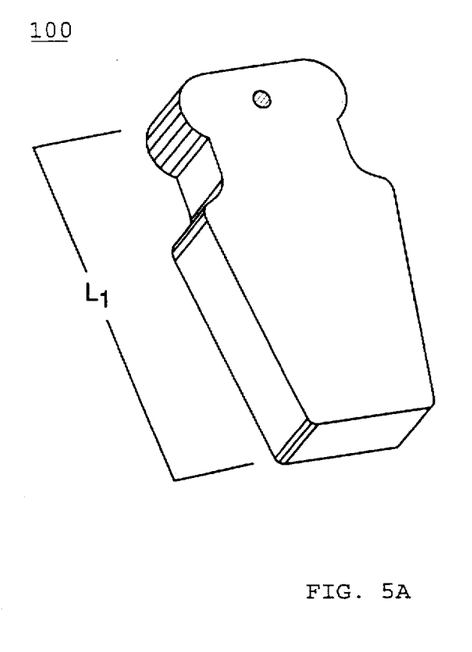
FIG. 5A is a front elevational view of an enlarged mouth prop.
Figure 5B:
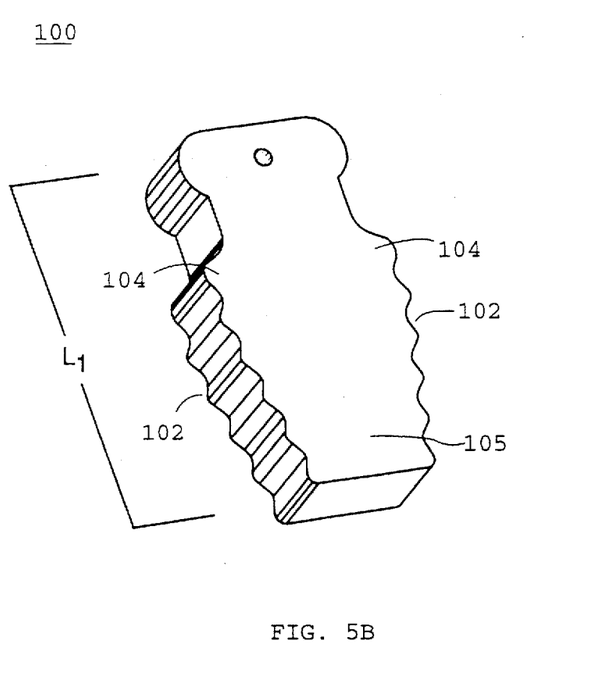
FIG. 5B is a from elevational view of the enlarged mouth prop having depressions in the side surfaces thereof.

FIG. 5A-5B show a mouth prop 100 having an enlarged length $L_1$ in comparison to mouth prop 70. Length $L_1$ of mouth prop 100 is in the range of about 1.25 inches to about 2.25 inches. The enlarged length provides an alternate placement for the hole through which a string or floss is placed to prevent the possibility of the mouth prop falling into the airway during dental procedures. The alternate placement away from the mouth may be necessary for patients with a sensitive gag reflex to enable the string to be farther away from the mouth. Mouth prop 100 can be formed with a plurality of depressions 102 on sides 104 for holding open the jaws of the patient and to provide a comfortable yet secure surface upon which to rest the teeth. Mouth prop 100 is formed of material 105. Material 105 can be formed of a material similar to material 62 described above. Mouth prop 100 can have a solid core.

In summary, the present invention has the advantage of providing a lightweight, inexpensive and disposable method of adapting devices for personal hygiene and professional oral care. A hygiene implement handle makes it easier for people with special needs to grip hygiene implements. The mouth prop allows care givers and oral care professionals to hold open the mouth of a person whom they are treating, while protecting their own fingers from closure of the teeth. The strength of the foam material and the rigid core ensures the device will not break apart or twist when the patient bites down on it. The mouth prop has a wedge shape to provide a secure yet comfortable surface upon which to rest the teeth.

While the invention has been described with reference to the preferred embodiment, this description is not intended to be limiting. It will be appreciated by those of ordinary skill in the art that modifications may be made without departing from the spirit and scope of the invention.

I claim:

1. A disposable mouth prop handle apparatus comprising:

an elongated handle having a first and second end;

a mouth prop longitudinally coupled to said first end of said handle, said mouth prop having a surface for supporting the teeth of a user of said mouth prop; and a rigid core continuously extending within said handle and said mouth prop, wherein said handle and said mouth prop are formed integrally to one another of a compressible foam material, said foam material surrounding said rigid core, the compressible foam material being rigid to withstand pressure from the teeth and providing comfort to a user of said mouth prop.

2. The mouth prop handle apparatus of claim 1 wherein said handle has a side surface and said handle has a plurality of depressions in said side surface of said handle.

3. The mouth prop handle apparatus of claim 2 wherein said mouth prop has a side surface and said mouth prop has a plurality of depressions in said side surface of said mouth prop.

4. The mouth prop handle apparatus of claim 3 wherein said mouth prop has a wedge shape with a larger and smaller end, the larger end of said wedge shape being closer to said first end of said handle than the smaller end of said wedge shape.

5. The mouth prop handle apparatus of claim 1 wherein said compressible foam material has a compression strength in the range of about 10 to about 100 pounds per square inch.

6. The mouth prop handle apparatus of claim 5 wherein said compressible foam material is selected from the group comprising polyethylene and polyolefin.

7. The mouth prop handle apparatus of claim 1 further comprising a flavorant in said compressible foam material.

* * * * *